(12) United States Patent
Bünger et al.

(10) Patent No.: US 7,981,899 B2
(45) Date of Patent: Jul. 19, 2011

(54) USE OF COMPATIBLE SOLUTES FOR INHIBITING THE RELEASE OF CERAMIDES

(75) Inventors: Joachim Bünger, Gross-Umstadt (DE); Jean Krutmann, Wagberg (DE)

(73) Assignee: Merck Patent GmbH, Darmstadt (DE)

( * ) Notice: Subject to any disclaimer, the term of this patent is extended or adjusted under 35 U.S.C. 154(b) by 2017 days.

(21) Appl. No.: 10/509,368

(22) PCT Filed: Mar. 3, 2003

(86) PCT No.: PCT/EP03/02146
§ 371 (c)(1),
(2), (4) Date: Sep. 28, 2004

(87) PCT Pub. No.: WO03/082239
PCT Pub. Date: Oct. 9, 2003

(65) Prior Publication Data
US 2005/0201955 A1 Sep. 15, 2005

(30) Foreign Application Priority Data
Mar. 28, 2002 (DE) ................................. 102 14 257

(51) Int. Cl.
*A61K 31/505* (2006.01)
*A61K 31/415* (2006.01)
(52) U.S. Cl. .................... 514/256; 514/269; 514/401
(58) Field of Classification Search ............ 424/401; 514/401, 256, 269
See application file for complete search history.

(56) References Cited

U.S. PATENT DOCUMENTS

| | | | |
|---|---|---|---|
| 2,649,397 A | 5/1950 | Ballard | |
| 4,346,105 A | 8/1982 | Sallmann et al. | |
| 4,529,587 A | 7/1985 | Green et al. | |
| 4,877,805 A | 10/1989 | Kligman et al. | |
| 5,047,409 A | 9/1991 | DiSchiena et al. | |
| 5,204,099 A | 4/1993 | Barbier et al. | |
| 5,403,845 A | 4/1995 | Dunbar et al. | |
| 5,476,852 A * | 12/1995 | Cauwenbergh | 514/254.07 |
| 5,665,366 A | 9/1997 | Rawlings et al. | |
| 5,738,858 A | 4/1998 | Burger | |
| 5,780,042 A | 7/1998 | Gers-Barlag et al. | |
| 5,789,414 A | 8/1998 | Lapidot et al. | |
| 5,827,508 A | 10/1998 | Tanner et al. | |
| 5,972,718 A | 10/1999 | Moghaddam et al. | |
| 6,001,838 A | 12/1999 | Stockhammer et al. | |
| 6,057,282 A | 5/2000 | Desai et al. | |
| 6,060,071 A | 5/2000 | Motitschke et al. | |
| 6,130,254 A * | 10/2000 | Fisher et al. | 514/725 |
| 6,153,176 A | 11/2000 | Kaleta et al. | |
| 6,267,973 B1 | 7/2001 | Motitschke et al. | |
| 6,403,112 B2 | 6/2002 | Motitschke et al. | |
| 6,551,917 B2 | 4/2003 | Cobbley et al. | |
| 6,602,514 B1 | 8/2003 | Bunger et al. | |
| 6,638,543 B2 | 10/2003 | Kang et al. | |
| 2002/0106337 A1* | 8/2002 | Deckers et al. | 424/59 |
| 2003/0114358 A1 | 6/2003 | Galinski et al. | |
| 2003/0157040 A1 | 8/2003 | Bunger et al. | |
| 2003/0190292 A1 | 10/2003 | Bunger et al. | |
| 2003/0198609 A1 | 10/2003 | Bunger et al. | |
| 2003/0199446 A1 | 10/2003 | Bunger et al. | |
| 2004/0043940 A1 | 3/2004 | Bunger et al. | |
| 2004/0047828 A1 | 3/2004 | Bunger et al. | |

FOREIGN PATENT DOCUMENTS

| | | |
|---|---|---|
| DE | 2 132 079 | 1/1973 |
| DE | 2 154 948 | 5/1973 |
| DE | 2614723 | 10/1977 |
| DE | 2746650 | 4/1979 |
| DE | 4244580 | 7/1994 |
| DE | 4342560 | 6/1995 |
| DE | 199 33 466 | 1/2000 |
| DE | 19933460 | 1/2000 |
| DE | 19933461 | 1/2000 |
| DE | 19933463 | 1/2000 |
| DE | 19933464 | 1/2000 |
| DE | 198 34 818 | 2/2000 |
| DE | 199 11 775 | 2/2000 |
| DE | 19834816 | 2/2000 |
| DE | 10006578 | 8/2001 |
| DE | 100 14 632 | 9/2001 |
| EP | 0 888 542 | 9/1983 |
| EP | 0 275 719 | 7/1988 |
| EP | 0 553 884 | 8/1993 |
| EP | 647469 | 4/1995 |
| EP | 0 671 161 | 9/1995 |
| EP | 0915167 | 5/1999 |
| EP | 1 125 583 | 8/2001 |
| GB | 1513659 | 6/1978 |
| GB | 2114886 | 9/1983 |
| JP | 02104577 | 4/1990 |
| JP | 3086867 | 11/1991 |

(Continued)

OTHER PUBLICATIONS

Mohammad, Taj, "Laser-induced In Vitro Isomerization of Urocanic Acid in UVA Region and the Origin of Excited Triplet State," Tetrahedron Letters, vol. 43, pp. 8897-8900 (2002).*
Beyer N et al: "Ectoin—A Innovative, Multi-Functional Active Substance for the Cosmetic Industry" SOFW-Journal Seifen, Oele Fette, Wachse, Verlag Fur Chemische Industrie, H. Ziolkowsky K.G. Augsburg, DE Bd. 126, Nr. 12, Dec. 2000, pp. 26,28-29.
Eisvogel M.: "Sun Protection With Anti-Ageing Merck Puts Ectoin to Work" Cossma, Nr. 4, 2001, pp. 32-33.
U.S. Appl. No. 08/355,275, Motitschke.
U.S. Appl. No. 08/746,253, Motitschke.
U.S. Appl. No. 09/744,766, Bunger et al.
U.S. Appl. No. 09/744,767, Bunger et al.
Galinski et al., "1,4,5,6-Tetrahydro-2-methyl-4-pyrimidinecarboxylic Acid," *Eur. J. Biochem.* 149:135-39 (1985).
Idson, B., "Dry Skin Moisturizing and Emolliency," *Cosmetics & Toiletries* 107:69-78 (1992).

(Continued)

*Primary Examiner* — Raymond J Henley, III
(74) *Attorney, Agent, or Firm* — Millen, White, Zelano & Branigan, P.C.

(57) ABSTRACT

Disclosed are the use of compatible solutes for inhibiting the release of ceramides or for the prophylaxis and protection of human skin against premature skin aging and for the prophylaxis and protection of human skin against wrinkling.

10 Claims, 4 Drawing Sheets

FOREIGN PATENT DOCUMENTS

| | | |
|---|---|---|
| JP | 3031265 | 12/1991 |
| JP | 9143167 | 6/1997 |
| WO | WO 94 04128 | 3/1994 |
| WO | WO 94/15923 | 7/1994 |
| WO | WO 96 17590 | 6/1996 |
| WO | WO 98 13020 | 4/1998 |
| WO | WO 0007558 | 2/2000 |
| WO | WO 0007560 | 2/2000 |
| WO | WO 00 76528 | 12/2000 |
| WO | WO 0158446 | 8/2001 |
| WO | WO 01 76572 | 10/2001 |
| WO | WO 0172263 | 10/2001 |
| WO | WO 0207522 | 1/2002 |
| WO | WO 03 007892 | 1/2003 |

OTHER PUBLICATIONS

Severin et al., "The Predominant Role of Recently Discovered Tetrahydropyrimidines for the Osmoadaptation of Halophilic Eubacteria," *Journal of General Microbiology* 138:1629-38 (1992).

Sauer T. et al., "Ectoine—Biotechnische produktion und moegliche anwendungsbereiche," Git Fachzeitschrift Fuer Das Laboratorium, vol. 39, No. 10, pp. 892-896, 1995.

Buenger J., "Neue wirkstoffklasse schuetzt und pflegt die haut. ectoine stabilisieren biopolymerstrukturen," Parfumerie und Kosmetik, vol. 79, No. 11, pp. 32-35, 1998.

Beyer N. et al., "Ectoin—a innovative multi-functional active substance for the cosmetic industry," SOFW Journal, vol. 126, No. 12, pp. 26, 28-29, 2000.

Krezel, I., "Antitumor activity of new derivatives of 1,3-diazaheterocycles," Pharmazie, vol. 53, No. 9, pp. 614-617, 1998.

Adams J.L. et al., "cis-4-Carboxy-6-(mercaptomethyl)-3,4,5,6-tetrahydropyrimidin-2(1H)-one, a potent inhibitor of mammalian dihydroorotase," J.Med.Chem., vol. 31, No. 7, pp. 1355-1359, 1988.

RonaCare Ectoin—The Cell Protection Factor, Merck KGaA.

Galinski at el., "The Kosmotropic (Structure-Forming) Effect of Compensatory Solutes", Comp. Biochem, Physiol. vol. 117A, No. 3, pp. 357-365, 1997.

Chemical Abstracts 132:170870, "Cosmetic compositions containing plant extracts having moisture-retaining effects", Doi et al. (Feb. 22, 2000).

Chemical Abstracts 129:179959, "Betaine-containing toothpaste relieves subjective symptoms of drymouth", Sondering et al. (1998).

* cited by examiner

USE OF COMPATIBLE SOLUTES FOR INHIBITING THE RELEASE OF CERAMIDES

The invention relates to the use of compatible solutes for inhibiting the release of ceramides or for the prophylaxis and protection of human skin against premature skin ageing and for the prophylaxis and protection of human skin against wrinkling.

Cell metabolism of human keratinocytes is influenced by exposure to UV light. Thus, for example, UVA irradiation and the formation of singlet oxygen causes the release of a so-called "second messenger" from the cell membrane. This second messenger activates transcription factor AP-2. Transcription factor AP-2 induces expression of pro-inflammatory genes.

The metabolic cascade effected, for example, by UV-induced release of ceramides, which are specific second messengers, results in increased synthesis of pro-inflammatory proteins and reactive oxygen species which can damage skin cells. This cell damage is an essential influencing factor for skin ageing, in particular premature skin ageing and wrinkling of the human skin.

The object is thus to combat skin-cell damage due to increased release of ceramides.

Surprisingly, it has now been found that compatible solutes are advantageously suitable for inhibiting the release of ceramides.

According to a common definition, compatible solutes are stress protection substances from extremely halophilic and halotolerant eubacteria, which accumulate them in large amounts through biosynthesis or effective transport mechanisms. These osmotically active substances prevent liquid outflow into the medium (drying out) and owe their name to the fact that they do not impair cell metabolism, even in high cytoplasmic concentration (up to about 2 molal), i.e. are compatible with metabolism. (according to: E. A. Galinski, M. Stein, B. Amendt, M. Kinder Comp. Biochem. Physiol., 117 (3) (1997) 357-365).

The invention thus relates to the use of one or more compounds selected from compatible solutes for inhibiting the release of ceramides and to the use of one or more compounds selected from compatible solutes for the prophylaxis and protection of human skin against premature skin ageing and to the use of one or more compounds selected from compatible solutes for the prophylaxis and protection of human skin against wrinkling.

The invention furthermore relates to the use of one or more compounds selected from compatible solutes for the preparation of compositions which are suitable for inhibiting the release of ceramides or are suitable for the prophylaxis and protection of human skin against premature skin ageing or for the prophylaxis and protection of human skin against wrinkling.

In the course of the present invention, it was found that compatible solutes inhibit the release of ceramides from membrane-bound sphingomyelin, which is induced, for example, by free radicals and UV light, in particular UV-A light.

Inhibiting the release of ceramides prevents the expression of matrix metalloproteinases. This in turn enables increased degradation of collagen fibres of the skin to be avoided.

In addition, inhibiting the release of ceramides prevents increased expression of pro-inflammatory proteins, in particular increased expression of genes, such as, for example, ICAM-1.

Compatible solutes inhibit the above-mentioned metabolic cascade, initiated, for example, by UV light, as early as the first reaction steps and thus prevent damage to the skin cells.

Compatible solutes inhibit the UV-induced release of ceramides from sphingomyelin and thus also the subsequent reaction steps of the metabolic cascade based on the release of ceramides.

In accordance with the invention, compatible solutes are advantageously suitable for protection of the collagen fibres of the skin. Compatible solutes are furthermore suitable for protection of the human skin against wrinkling.

In accordance with the invention, compatible solutes are in addition advantageously suitable for protection against the formation of pro-inflammatory substances and reactive oxygen species resulting therefrom.

Long-wave ultraviolet radiation (UVA 320-400 nm) is one of the most important noxae to which the human skin is exposed under physiological conditions and for therapeutic or cosmetic reasons. UVA radiation is crucially involved in the pathogenesis of photodermatoses (for example polymorphic photodermatosis, lupus erythematodes; light urticaria, photoallergic and phototoxic reactions), premature and accelerated skin ageing (photoageing) and photocarcinogenesis. For these health-damaging effects, regulation of the expression of genes in human skin cells is of fundamental importance. In addition, very recent papers indicate that the generation of-mutations in mitochondrial DNA in these cells is of equally crucial importance for the premature ageing process of human skin initiated by UVA radiation. The mitochondria contain their own genomic material which encodes for proteins involved in oxidative phosphorylation. It is located in the region of the inner mitochondrial membrane in the form of a circular DNA molecule and is thus exposed to oxidative stress to an increased extent. The resultant mutations of mitochondrial DNA are important not only for the pathogenesis of degenerative diseases, but also for cell and tissue ageing. Thus, normal healthy tissue has an increasing content of mitochondrial DNA mutations depending on its age. This is associated with a reduction in its ability to undergo oxidative phosphorylation. UVA radiation is a potent inductor of oxidative stress and is therefore capable of causing mitochondrial DNA mutations in the skin. Thus, photoaged skin correspondingly has a significantly increased content of mitochondrial DNA mutations compared with light-protected skin. In addition, it has recently been shown that repetitive UVA irradiation of human fibroblasts results in time- and dose-dependent generation of mitochondrial DNA mutations.

The use according to the invention of compatible solutes is preferably suitable for people with photodermatoses, in particular for people with photodermatoses selected from polymorphic photodermatosis, lupus erythematodes and light urticaria.

Compatible solutes which are preferred in accordance with the invention are selected from sugars and polyols, such as, for example, trehalose, glycerol, glycosyl glycerol, β-mannosyl glycerate (firoin), β-mannosyl-glyceramide (firoin A), di-myo-inositol phosphate (DIP), cyclic 2,3-diphosphoglycerate (cDPG), 1,1-diglycerol phosphate (DGP) and dimannosyl diinositol phosphate (DMIP), and amino acids and amino acid derivatives, such as, for example, the betaines, preferably glycine betaine, proline betaine or glutamate betaine, alanine, proline, glutamine, N-acetyl lysine, glutamine 1-amide, taurine, choline, choline O-sulfate, carnitine, arsenobetaine, crotonobetaine, dimethyl sulfonioacetate, dimethyl sulfopropionate, homobetaine, trimethylamine N-oxide and ectoins.

Particularly preferred compatible solutes are selected from the compounds of the formulae Ia and Ib

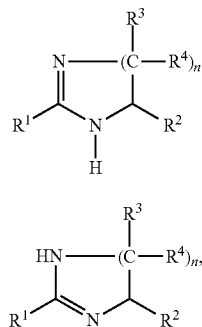

the physiologically tolerated salts of the compounds of the formulae Ia and Ib, and the stereoisomeric forms of the compounds of the formulae Ia and Ib, where
$R^1$ is H or alkyl,
$R^2$ is H, COOH, COO-alkyl or CO—NH—$R^5$,
$R^3$ and $R^4$ are each, independently of one another, H or OH,
n is 1, 2 or 3,
alkyl is an alkyl radical having from 1 to 4 carbon atoms, and
$R^5$ is H, alkyl; an amino acid residue, a dipeptide radical or a tripeptide radical.

For the purposes of the present invention, all compounds above and below selected from the compounds of the formulae Ia and Ib, the physiologically tolerated salts of the compounds of the formulae Ia and Ib, and the stereoisomeric forms of the compounds of the formulae Ia and Ib are referred to as "ectoin or ectoin derivatives".

Ectoin and ectoin derivatives are low-molecular-weight, cyclic amino acid derivatives which can be isolated from various halophilic microorganisms or prepared synthetically. Both ectoin and hydroxyectoin have the advantage of not reacting with cell metabolism.

The compounds selected from the compounds of the formulae Ia and Ib, the physiologically tolerated salts of the compounds of the formulae Ia and Ib and the stereoisomeric forms of the compounds of the formulae Ia and Ib can be present in the compositions in the form of optical isomers, diastereomers, racemates, zwitterions, cations or mixtures thereof. Of the compounds selected from the compounds of the formulae Ia and Ib, the physiologically tolerated salts of the compounds of the formulae Ia and Ib and the stereoisomeric forms of the compounds of the formulae Ia and Ib, preference is given to the compounds in which $R^1$ is H or $CH_3$, $R^2$ is H or COOH, $R^3$ and $R^4$ are each, independently of one another, H or OH, and n is 2. Of the compounds selected from the compounds of the formulae Ia and Ib, the physiologically tolerated salts of the compounds of the formulae Ia and Ib and the stereoisomeric forms of the compounds of the formulae Ia and Ib, particular preference is given to the compounds (S)-1,4,5,6-tetrahydro-2-methyl-4-pyrimidinecarboxylic acid (ectoin) and (S,S)-1,4,5,6-tetrahydro-5-hydroxy-2-methyl-4-pyrimidinecarboxylic acid (hydroxyectoin).

The amino acid residues mentioned under the radical $R^5$ of the compounds of the formulae Ia and Ib are derived from the corresponding amino acids. The term "amino acid" is taken to mean the stereoisomeric forms, for example D and L forms, of the following compounds: alanine, β-alanine, arginine, asparagine, aspartic acid, cysteine, glutamine, glutamic acid, glycine, histidine, isoleucine, leucine, lysine, methionine, phenylalanine, serine, threonine, tryptophan, tyrosine, valine, γ-aminobutyrate, $N^\epsilon$-acetyllysine, $N^\delta$-acetylornithine, $N^\gamma$-acetyldiaminobutyrate and $N^\alpha$-acetyl-diaminobutyrate. L-amino acids are preferred. The residues of the following amino acids are preferred: alanine, β-alanine, asparagine, aspartic acid, glutamine, glutamic acid, glycine, serine, threonine, valine, γ-aminobutyrate, $N^\epsilon$-acetyllysine, $N^\delta$-acetylornithine, $N^\gamma$-acetyldiamino-butyrate and $N^\alpha$-acetyldiaminobutyrate.

The di- and tripeptide radicals mentioned under the radical $R^5$ of the compounds of the formulae Ia and Ib are acid amides in terms of their chemical nature and decompose on hydrolysis to give 2 or 3 amino acids. The amino acids in the di- and tripeptide radicals are bonded to one another by amide bonds. Preferred di- and tripeptide radicals are built up from the preferred amino acids.

The alkyl groups mentioned under the radicals $R^1$, $R^2$ and $R^5$ in the compounds of the formulae Ia and Ib include the methyl group $CH_3$, the ethyl group $C_2H_5$, the propyl groups $CH_2CH_2CH_3$ and $CH(CH_3)_2$ and the butyl groups $CH_2CH_2CH_2CH_3$, $H_3CCHCH_2CH_3$, $CH_2CH(CH_3)_2$ and $C(CH_3)_3$. The preferred alkyl group is the methyl group.

Preferred physiologically tolerated salts of the compounds of the formulae Ia and Ib are, for example, alkali metal, alkaline earth metal or ammonium salts, such as Na, K, Mg or Ca salts, and salts derived from the organic bases triethylamine or tris(2-hydroxyethyl)amine. Further preferred physiologically tolerated salts of the compounds of the formulae Ia and Ib arise through reaction with inorganic acids, such as hydrochloric acid, sulfuric acid and phosphoric acid, or with organic carboxylic or sulfonic acids, such as acetic acid, citric acid, benzoic acid, maleic acid, fumaric acid, tartaric acid and p-toluenesulfonic acid.

Compounds of the formulae Ia and Ib in which basic and acidic groups, such as carboxyl or amino groups, are present in equal number form internal salts.

The preparation of the compounds of the formulae Ia and Ib is described in the literature (DE 43 42 560). (S)-1,4,5,6-Tetrahydro-2-methyl-4-pyrimidinecarboxylic acid or (S,S)-1,4,5,6-tetrahydro-5-hydroxy-2-methyl-4-pyrimidinecarboxylic acid can also be obtained by microbiological methods (Severin et al., J. Gen. Microb. 138 (1992) 1629-1638).

The use of compounds selected from the compounds of the formulae Ia and Ib for cosmetic and pharmaceutical purposes is already known.

For example, WO 94/15923 describes that (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid can be used for the preparation of a cosmetic composition or a medicament, for example for the treatment of skin diseases.

Furthermore, DE 43 42 560 describes the use of ectoin and ectoin derivatives as moisturisers in cosmetic products. These products are suitable, for example, for the care of aged, dry or irritated skin.

Furthermore, DE 199 33 466 describes that ectoin and derivatives, such as hydroxyectoin, can be employed as antioxidants and free-radical scavengers in cosmetic and dermatological compositions. The compositions can be used for the treatment and/or prophylaxis of skin ageing caused by oxidative stress and of inflammatory reactions.

Further applications of ectoin and ectoin derivatives in cosmetic formulations are described, for example, in WO 00/07558, WO 00/07559 and WO 00/07560, such as, for example, the care and prophylaxis of dry and/or flaky skin, protection of the human skin against dryness and/or high salt concentrations, protection of cells, proteins and/or biomembranes of the human skin, protection of the microflora of the human skin, stabilisation of the skin barrier and protection and stabilisation of nucleic acids of human skin cells.

However, it was hitherto not known that the compounds selected from compatible solutes, such as, for example, the compounds of the formulae Ia and Ib, the physiologically tolerated salts of the compounds of the formulae Ia and Ib and the stereoisomeric forms of the compounds of the formulae Ia and Ib, are advantageously suitable for inhibiting the release of ceramides.

The use according to the invention of the compounds selected from compatible solutes preferably takes place in such a way that the said compounds are in the form of a cosmetic, dermatological or medicament composition, in particular in a corresponding formulation.

The proportion of the compounds selected from the compounds of the compatible solutes, in particular the compounds of the formulae Ia and Ib, the physiologically tolerated salts of the compounds of the formulae Ia and Ib and the stereoisomeric forms of the compounds of the formulae Ia and Ib in the cosmetic, dermatological or medicament composition, is preferably from 0.001 to 50% by weight, particularly preferably from 0.01 to 10% by weight and especially preferably from 0.1 to 10% by weight, based on the composition as a whole. The proportion of the said compounds in the composition is very especially preferably from 0.1 to 5% by weight, based on the composition as a whole.

Besides the compatible solutes, the compositions may also comprise further cosmetic, dermatological or pharmaceutical active ingredients.

The compositions may comprise one or more antioxidants. The compositions may comprise all common antioxidants. In this connection, there are many proven substances known from the specialist literature which can be used as antioxidants, for example flavonoids, coumaranones, amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, -hexa- and heptathionine sulfoximine) in very low tolerated doses (for example pmol to μmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example, vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide), metabisulfite salts, sulfite salts or hydrogensulfite salts.

Mixtures of antioxidants are likewise suitable for use in the compositions. Known and commercial mixtures are, for example, mixtures comprising, as active ingredients, lecithin, L-(+)-ascorbyl palmitate and citric acid (for example OXYNEX® AP), natural tocopherols, L-(+)-ascorbyl palmitate, L-(+)-ascorbic acid and citric acid (for example OXYNEX® K LIQUID), tocopherol extracts from natural sources, L-(+)-ascorbyl palmitate, L-(+)-ascorbic acid and citric acid (for example OXYNEX® L LIQUID), DL-α-tocopherol, L-(+)-ascorbyl palmitate, citric acid and lecithin (for example OXYNEX® LM) or butylhydroxytoluene (BHT), L-(+)-ascorbyl palmitate and citric acid (for example OXYNEX® 2004).

A further suitable antioxidant mixture can consist, for example, of, inter alia, emblicanin A, emblicanin B, puniglucinin and pendunculagin, as described, for example, in WO 00/48551 under the name CAPROS™ (for example EMBLICA™).

In a preferred embodiment of the invention, the composition comprises one or more compounds selected from flavonoids and/or coumaranones.

Flavonoids are taken to mean the glycosides of flavonones, flavones, 3-hydroxyflavones (=flavonols), aurones, isoflavones and rotenoids [Römpp Chemie Lexikon [Römpp's Lexicon of Chemistry], Volume 9, 1993]. For the purposes of the present invention, however, this term is also taken to mean the aglycones, i.e. the sugar-free constituents, and the derivatives of the flavonoids and aglycones. For the purposes of the present invention, the term flavonoid is furthermore also taken to mean anthocyanidine (cyanidine). For the purposes of the present invention, the term coumaranones is also taken to mean derivatives thereof.

Preferred flavonoids are derived from flavonones, flavones, 3-hydroxyflavones, aurones and isoflavones, in particular from flavonones, flavones, 3-hydroxyflavones and aurones.

The flavonoids are preferably selected from the following compounds: 4,6,3',4'-tetrahydroxyaurone, quercetin, rutin, isoquercetin, eriodictyol, taxifolin, luteolin, trishydroxyethylquercetin(troxequercetin), trishydroxyethylrutin(troxerutin), trishydroxyethylisoquercetin(troxeisoquercetin), trishydroxyethylluteolin(troxeluteolin), α-glycosylrutin, tiliroside and the sulfates and phosphates thereof. Of the flavonoids, particular preference is given to rutin and troxerutin.

Of the coumaranones, preference is given to 4,6,3',4'-tetrahydroxybenzyl-3-coumaranone.

In a further preferred embodiment of the invention, in particular if the water solubility of the flavonoids and/or coumaranones is to be increased, a polar group, for example, in each case independently of one another, a sulfate or phosphate group, is bonded to one or more hydroxyl groups of these compounds. Suitable counterions are, for example, the ions of the alkali or alkaline earth metals, these being selected, for example, from sodium and potassium.

Many flavonoids and coumaranones are, for example, naturally occurring. If the composition comprises such compounds, they may also be obtained by extraction of corresponding plants and either purified as a single substance or alternatively introduced into the composition in the form of the extract, which may, if necessary, have been refined further.

The proportion of the one or more compounds selected from flavonoids and coumaranones in the composition is preferably from 0.001 to 5% by weight, particularly preferably from 0.01 to 2% by weight, based on the composition as a whole.

In a further preferred embodiment of the invention, the composition comprises one or more antioxidants selected from the substances citric acid, lactic acid, malic acid, EDTA, butylhydroxytoluene, ascorbic acid, ascorbyl palmitate, magnesium ascorbyl phosphate, ascorbyl acetate, tocopherol, tocopherol acetate, and metabisulfite, sulfite or hydrogensulfite salts selected from alkali metal salts, such as sodium and potassium salts, basic metal salts and ammonium salts.

In a further preferred embodiment of the invention, the composition comprises antioxidant mixtures, such as, for example, Emblica™.

The proportion of the one or more antioxidants in the composition is preferably from 0.001 to 5% by weight, particularly preferably from 0.01 to 2% by weight, based on the composition as a whole.

The compositions may comprise one or more UV filters. Suitable organic UV filters are all UVA and UVB filters known to the person skilled in the art. For both UV ranges, there are many proven substances which are known from the specialist literature, for example
benzylidenecamphor derivatives, such as
    3-(4'-methylbenzylidene)-dl-camphor (for example EUSOLEX® 6300),
    3-benzylidenecamphor (for example MEXORYL® SD),
    polymers of N-{(2 and 4)-[(2-oxoborn-3-ylidene)methyl] benzyl}acrylamide (CAS No. 113783-61-2, for example MEXORYL® SW),
    N,N,N-trimethyl-4-(2-oxoborn-3-ylidenemethyl) anilinium methyisulfate (CAS No. 52793-97-2, for example MEXORYL® SK) or
    α-(2-oxoborn-3-ylidene)toluene-4-sulfonic acid (CAS No. 56039-58-8, for example MEXORYL® SL),
benzoyl- or dibenzoylmethanes, such as
    1-(4-tert-butylphenyl)-3-(4-methoxyphenyl)propane-1,3-dione (for example EUSOLEX® 9020) or
    4-isopropyldibenzoylmethane (for example EUSOLEX® 8020),
benzophenones, such as
    2-hydroxy-4-methoxybenzophenone (for example EUSOLEX® 4360) or
    2-hydroxy-4-methoxybenzophenone-5-sulfonic acid and its sodium salt (for example UVINUL® MS-40),
methoxycinnamic acid esters, such as
    octyl methoxycinnamate (for example EUSOLEX® 2292) or
    isopentyl 4-methoxycinnamate, for example as a mixture of the isomers (for example NEO HELIOPAN® E 1000),
salicylate derivatives, such as
    2-ethylhexyl salicylate (for example EUSOLEX®OS),
    4-isopropylbenzyl salicylate (for example MEGASOL®) or
    3,3,5-trimethylcyclohexyl salicylate (for example EUSOLEX®HMS),
4-aminobenzoic acid and derivatives, such as
    4-aminobenzoic acid,
    2-ethylhexyl 4-(dimethylamino)benzoate (for example EUSOLEX®6007) or
    ethoxylated ethyl 4-aminobenzoate (for example UVINUL®P25),
and further substances, such as
    2-ethylhexyl 2-cyano-3,3-diphenylacrylate (for example EUSOLEX® OCR),
    2-phenylbenzimidazole-5-sulfonic acid and potassium, sodium and triethanolamine salts thereof (for example EUSOLEX®232),
    3,3'-(1,4-phenylenedimethylene)bis(7,7-dimethyl-2-oxobicyclo[2.2.1]hept-1-ylmethanesulfonic acid and salts thereof (for example MEXORYL®SX),
    2,4,6-trianilino-(p-carbo-2'-ethylhexyl-1'-oxy)-1,3,5-triazine (for example UVINUL® T 150) or
    hexyl 2-(4-diethylamino-2-hydroxybenzoyl)benzoate (for example UVINUL®UVA Plus, BASF).

The compounds listed should merely be regarded as examples. It is of course also possible to use other UV filters.

These organic UV filters are generally incorporated into the compositions in an amount of from 0.5 to 10% by weight, preferably 1-8% by weight.

Further suitable organic UV filters are, for example,
    2-(2H-benzotriazol-2-yl)-4-methyl-6-(2-methyl-3-(1,3,3,3-tetramethyl-1-(trimethylsilyloxy)disiloxanyl)propyl) phenol (for example SILATRIZOLE®),
    2-ethylhexy4,4'-[(6-[4-((1,1-dimethylethyl)aminocarbonyl)phenylamino]-1,3,5-triazine-2,4-diyl)diimino]bis (benzoate)(CAS No. 154702-15-5, for example UVASORB®HEB),
    α-(trimethylsilyl)-ω-[trimethylsilyl)oxy]poly[oxy(dimethyl [and about 6% of methyl[2-[p-[2,2-bis(ethoxycarbonyl]vinyl]phenoxyl-1-methyleneethyl] and about 1.5% of methyl[3-[p-[2,2-bis(ethoxycarbonyl)vinyl) phenoxy)propenyl] and from 0.1 to 0.4% of (methylhydrogen]silylene]] (n≈60) (CAS No. 207 574-74-1, for example Parsol SLX),
    2,2'-methylenebis(6-(2H-benzotriazol-2-yl)-4-(1,1,3,3-tetramethylbutyl)phenol) (CAS No. 103 597-45-1, for example Tinosorb M),
    2,2'-(1,4-phenylene)bis(1H-benzimidazole-4,6-disulfonic acid, monosodium salt) (CAS No. 180 898-37-7, for example Neo Heliopan AP),
    2,4-bis{(4-(2-ethylhexyloxy)-2-hydroxy]phenyl}-6-(4-methoxyphenyl)-1,3,5-triazine (CAS No. 187 393-00-6, for example Tinosorb S) or
    2,2'-(1,4-phenylene)bis(1H-benzimidazole-5-sulfonic acid) and potassium, sodium and triethanolamine salts thereof.

These organic UV filters are generally incorporated into the compositions in an amount of from 0.5 to 20% by weight, preferably in an amount of from 1 to 15% by weight and particularly preferably in amounts of from 2 to 8% by weight per individual substance.

Conceivable inorganic UV filters are those from the group consisting of titanium dioxides, such as, for example, coated titanium dioxide (for example EUSOLEX® T-2000, EUSOLEX® T-AQUA), zinc oxides (for example SACHTOTEC®), iron oxides and also cerium oxides. These inorganic UV filters are generally incorporated into the compositions in an amount of from 0.5 to 20% by weight, preferably from 2 to 10% by weight.

If different inorganic or organic UV filters are employed, these can be used in virtually any desired ratios to one another. The ratios of the individual substances to one another are usually in the range 1:10-10:1, preferably in the range 1:5-5:1 and particularly preferably in the range 1:2-2:1. If UV-A filters are employed alongside UV-B filters, it is advantageous for most applications if the proportion of UV-B filters predominates and the ratio of UV-A filters to UV-B filters is in the range from 1:1 to 1:10.

Preferred compounds having UV-filtering properties which are used in the compositions are 3-(4'-methylbenzylidene)-dl-camphor, 1-(4-tert-butyl-phenyl)-3-(4-methoxyphenyl)propane-1,3-dione, 4-isopropyldibenzoyl-methane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and potassium, sodium and triethanolamine salts thereof, as well as coated titanium dioxide.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in compositions, such as, for example, cosmetic formulations. Encapsulation of these filters or compounds which impair the photostability of these filters, such as, for example, the above-mentioned cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables formulation problems caused by the interaction of individual formulation-constituents with one another, such as crystallisation processes, precipitation and agglomerate formation, to be avoided since the interaction is suppressed.

It is therefore preferred for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in the compositions in amounts which ensure that the encapsulated UV filters are present in the composition in the above-indicated amounts.

The composition may also comprise one or more amino acids or pharmaceutically tolerated salts thereof. Preferred amino acids are selected from the group of compounds consisting of alanine, valine, leucine, isoleucine, proline, methionine, phenylalanine, tryptophan, glycine, serine, threonine, cysteine, tyrosine,-asparagine, glutamine, lysine, arginine and histidine.

If the composition comprises amino acids, the proportion of the amino acids or pharmaceutically tolerated salts thereof in the composition is preferably from 0.1 to 10% by weight, particularly preferably from 0.1 to 8% by weight and especially preferably from 0.2 to 5% by weight, based on the composition as a whole. The proportion of the amino acids or pharmaceutically tolerated salts thereof in the composition is very especially preferably from 0.2 to 2% by weight, based on the composition as a whole.

The ingredients can be incorporated into the compositions in a conventional manner. Suitable formulations are those for external application, for example as a cream, lotion, gel or as a solution which can be sprayed onto the skin. It is preferred here for the formulation to comprise at least one oil phase and at least one water phase.

Application forms of the formulations which may be mentioned are, for example: solutions, emulsions, PIT emulsions, suspensions, ointments, gels, creams, lotions, sprays and aerosols. Further application forms are, for example, sticks. Any desired conventional carriers, adjuvants and optionally further active ingredients may be added to the formulation.

Preferred adjuvants originate from the group consisting of preservatives, antioxidants, stabilisers, solubilisers, vitamins, colorants, odour improvers, film formers, thickeners and humectants.

Solutions and emulsions can comprise the conventional carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, groundnut oil, maize oil, olive oil, castor oil and sesame oil, glycerol fatty acid esters, polyethylene glycols and fatty acid esters of sorbitan, or mixtures of these substances.

The emulsions can exist in various forms. Thus, they can be, for example, an emulsion or microemulsion of the water-in-oil (W/O) type or of the oil-in-water (O/W) type, or a multiple emulsion, for example of the water-in-oil-in-water (W/O/W) type.

The formulations may also be in the form of emulsifier-free, disperse compositions. They can be, for example, hydrodispersions or Pickering emulsions.

Suspensions can comprise the conventional carriers, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Pastes, ointments, gels and creams can comprise the conventional carriers, for example animal and vegetable fats, waxes, paraffins, starch, tragacanth, cellulose derivatives, polyethylene glycols, silicones, bentonites, silicic acid, talc and zinc oxide, or mixtures of these substances.

Face and body oils can comprise the conventional carriers, such as synthetic oils, such as fatty acid esters, fatty alcohols, silicone oils, natural oils, such as vegetable oils and oily plant extracts, paraffin oils, lanolin oils, or mixtures of these substances.

Sprays can comprise the conventional propellants, for example chlorofluorocarbons, propane/butane or dimethyl ether.

Further typical cosmetic application forms are, for example, make-up, such as, for example, emulsion make-up, and sunscreen, pre-sun and after-sun preparations.

The formulation is in various administration forms that are usually used for this application. Thus, it may, in particular, be in the form of a lotion or emulsion, such as a cream or milk (O/W, W/O, O/W/O, W/O/W), in the form of oily-alcoholic, oily-aqueous or aqueous-alcoholic gels or solutions, in the form of solid sticks or may be formulated as an aerosol.

The formulation can comprise adjuvants which are usually used in compositions of this type, such as, for example, thickeners, plasticisers, humectants, interface-active agents, emulsifiers, preservatives, antifoaming agents, perfumes, waxes, lanolin, propellants, dyes and/or pigments which colour the agent itself or the skin, and other ingredients usually used in cosmetics, dermatology or pharmacy.

The dispersant or solubiliser used can be an oil, wax or other fatty body, a lower monoalcohol or a lower polyol, or mixtures thereof. The particularly preferred monoalcohols or polyols include ethanol, i-propanol, propylene glycol, glycerol and sorbitol.

A preferred embodiment of the invention is an emulsion which is in the form of a cream or milk and comprises fatty alcohols, fatty acids, fatty acid esters, in particular triglycerides of fatty acids, lanolin, natural or synthetic oils or waxes and emulsifiers in the presence of water.

Further preferred embodiments are oily lotions based-on natural or synthetic oils and waxes, lanolin, fatty acid esters, in particular triglycerides of fatty acids, or oily/alcoholic lotions based on a lower alcohol, such as ethanol, or a glycol, such as propylene glycol, and/or a polyol, such as glycerol, and oils, waxes and fatty acid esters, such as triglycerides of fatty acids.

The formulation may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty bodies.

If a composition is formulated as an aerosol, the conventional propellants, such as alkanes, fluoroalkanes and chlorofluoroalkanes, are generally used.

The compositions as described above are applied to the skin.

Even without further comments, it is assumed that a person skilled in the art will be able to utilise the above description in its broadest scope. The preferred embodiments should therefore merely be regarded as descriptive disclosure which is absolutely not limiting in any way.

The complete disclosure content of all applications and publications mentioned above and below is incorporated into this application by way of reference.

The compositions can be prepared with the aid of techniques which are well known to the person skilled in the art.

All compounds or components which can be used in the compositions are either known and commercially available or can be isolated or prepared by methods which are well known to the person skilled in the art and are described in the literature (for example in standard works, such as Houben-Weyl, Methoden der organischen Chemie [Methods of Organic Chemistry], Georg-Thieme-Verlag, Stuttgart).

The following examples are intended to illustrate the present invention. However, they should in no way be regarded as limiting.

EXAMPLE A

Protective Action of RONACARE™ Ectoin

Normal human keratinocytes which are left untreated or have been treated with a 2 mM solution of RONACARE™ ectoin for 24 hours are subjected to a UV-A radiation dose of 30 J/cm$^2$ (wavelength of the UV-A radiation: 340-400 nm). It was previously found that this dose induces the cascade described above without influencing the living cell count. The cells are harvested 1 hour after irradiation (=maximum UV-A-induced second messenger formation). The release of the second messenger was determined.

The results are shown in Table 1 below:

TABLE 1

| Release of second messenger in UV-A-irradiated skin | |
|---|---|
| Sample | Increase in second messenger [ng] |
| Untreated/unirradiated | 6.01 |
| Untreated/irradiated | 12.90 |
| Ectoin-treated/irradiated | 5.65 |

The experiment shows that RONACARE™ ectoin inhibits the UV-A-induced release of the second messenger. The above-mentioned cascade is interrupted by the reduction in the concentration of second messenger. This enables harmful influences and damage to skin cells and collagen fibres owing to the expression of matrix metalloproteinases and pro-inflammatory genes to be avoided.

EXAMPLE B

Protective Action of RONACARE™Ectoin

EXAMPLE B1

Inhibition of UV-A-induced Ceramide Formation

The concentration of a second messenger (ceramide) in UVA-irradiated normal human keratinocytes which have either been pretreated with 1 mM RONACARE™ ectoin or are untreated compared with unirradiated keratinocytes is measured using a quantitative HPTLC method. (A) Un-pretreated control, (B) pre-incubated only with the cell medium for 24 hours, (C) pre-incubated with 1 mM RONACARE™ ectoin for 24 hours. The cells pre-treated in this way are irradiated with a single dose of UVA of 30 J/cm$^2$ (radiation source: Sellamed 24000). The cells are "harvested" 1 hour after irradiation, a lipid extraction is carried out, and the concentration of the second messenger is determined by quantitative HPTLC. Methodological details are given in Grether-Beck Set al., EMBO J 19: 5793-5800, 2000. FIG. 1 shows the data for each of three independent experiments. The data are shown as histograms of ectoin (mM) against ceramide (ng). It is found that treatment of cells with 1 mM ectoin completely suppresses ceramide formation induced by UVA radiation.

EXAMPLE B2

Inhibition of UV-A-induced AP-2 Activation

The determination of the activation of transcription factor AP-2 is carried out with the aid of gel electrophoresis mobility shift assays (GEMSA). To this end, a nucleus extract (according to J.D. Dignam, P.L.Martin, B.S. Skastry, R.G.G. Roeder, Methods Enzymol 101 (1983) 582-598) of human keratinocytes which had previously been irradiated for 1 hour with 30 J/cm² of UV-A light is incubated in comparison with an unirradiated control with the consensus oligonucleotide sequence of ICAM-1 promoter (in accordance with G.G. Stade, G. Messer, G. Riethmüller, J.P. Johannson; Immunobiology 182 (1990) 79-87). The amount of bound AP-2 is subsequently determined by means of GEMSA. (A) Un-pretreated, unirradiated control, (B) pre-incubated with 1 mM RONACARE™ ectoin for 24 hours and irradiated with a single dose of 30 J/cm², or (C) pre-incubated only with the cell medium for 24 hours and irradiated with 30 J/cm². The data for two experiments are shown in FIG. 2. The UVA irradiation results in activation of transcription factor AP-2 after UVA exposure. It is found that this activation can be suppressed virtually completely by pretreatment of the cells with 1 mM ectoin.

EXAMPLE B3

Inhibition of UV-A-induced ICAM-1 Expression

The expression of ICAM-1 is measured using differential reverse transcriptase PCR (RT-PCR) and the kit from Applied Biosystem. In order to take into account the normal variations in gene expression of skin cells, the ICAM-1 expression is compared with the housekeeping gene β-actin formed constitutively. Semiquantitative analysis of the RT-PCR is carried out by ion exchange chromatography using a UV spectrophotometer (A260). (A) Un-pretreated, irradiated control, (B) pre-incubated with 1 mM RONACARE™ ectoin for 24 hours and irradiated with a single dose of 30 J/cm², or (C) pre-incubated with 1 mM ectoin for 24 hours, unirradiated. Data obtained in two independent experiments are shown in FIG. 3. The UVA radiation induces an increase in ICAM-1 expression. The pretreatment of keratinocytes with 1 mM ectoin can virtually completely eliminate ICAM-1 induction induced by UVA radiation at all points in time.

EXAMPLE B4

Effect of Ectoin on UVA Radiation-induced Formation of Mitochondrial DNA Mutations Dermal human fibroblasts are cultivated in Eagle minimal medium. The cells are irradiated three times daily with 8 J/cm² of UVA on four successive days over a total of three weeks. The mt-DNA is then extracted and amplified using PCR. Further details on the method are described in detail in M. Berneburg, S. Grether-Beck, V. Kürten, Th. Ruzicka, K. Briviba, H. Sies, J. Krutmann, J Biol Chem 274 (1999) 15345-15349 and M. Berneburg, N. Gattermann, H. Stege, M. Grewe, K. Vogelsang, Th. Ruzicka, J. Krutmann, Photobiol. 66 (1997) 271-275. FIG. 4 shows the agarose gel of the reference fragment duplicated by means of PCR for representation of the common deletion as an indication of extensive UV-A-induced DNA mutations in primary human skin fibroblasts. Pretreatment of the fibroblasts with 1 mM RONACARE™ ectoin prevented the formation of mt-DNA mutations, as can be seen from direct comparison.

FORMULATION EXAMPLES

Example 1

Sunscreen Gel

| Raw material | INCI | % by wt. |
|---|---|---|
| A Sepigel 305 | (1) LAURETH-7, POLYACRYLAMIDE, C13-C14 ISOPARAFFIN | 2.0 |
| Phenonip | (2) PHENOXYETHANOL, BUTYLPARABEN, ETHYLPARABEN, PROPYLPARABEN, METHYLPARABEN | 0.7 |
| Water, demineralised | AQUA (WATER) | 30.0 |
| B RONACARE ™ ectoin | (3) ECTOIN | 0.3 |
| Glycerol (87% extra pure) | (3) GLYCERIN | 2.0 |
| Water, demineralised | AQUA (WATER) | 45.0 |
| C EUSOLEX ® UV-PEARLS ™ OMC | (3) AQUA (WATER), ETHYLHEXYL METHOXYCINNAMATE, SILICA, PVP, CHLORPHENESIN, BHT | 20.0 |

Preparation:
For the preparation of phase A, Sepigel 305 is mixed intimately with water and preservative. Phase B is dissolved and incorporated into phase A. The EUSOLEX ® UV-PEARLS ™ OMC are added with stirring, and the pH adjusted to 5 using citric acid.
Notes:
Viscosity 14,000 mPas (Brookfield LV, spindle 4, 12 rpm) at 25° C.

Sources of supply:
(1) Seppic
(2) Nipa Laboratorien GmbH
(3) MERCK KGAA/RONA ®

Example 2

Sunscreen Lotion for Sensitive Skin

| Raw material | INCI | % by wt. |
|---|---|---|
| A EUSOLEX ® T-S | (1) TITANIUM DIOXIDE, ALUMINA, STEARIC ACID | 10.0 |
| Arlacel P135 | (2) PEG-30 DIPOLYHYDROXYSTEARATE | 2.0 |
| Cetiol A | (3) HEXYL LAURATE | 12.0 |
| Arlamol S 7 | (2) CYCLOMETHICONE, PPG-15 STEARYL ETHER | 6.0 |
| Pecosil PS-100 | (4) DIMETHICONE COPOLYOL PHOSPHATE | 0.5 |
| B RONACARE ™ ectoin | (1) ECTOIN | 0.3 |
| Magnesium sulfate | (1) MAGNESIUM SULFATE | 0.7 |
| Glycerol (87% extra pure) | (1) GLYCERIN | 3.0 |
| Titriplex III | (1) DISODIUM EDTA | 0.05 |
| Water, demineralised | AQUA (WATER) | 44.75 |
| C EUSOLEX ® UV-PEARLS ™ OMC | (1) AQUA (WATER), ETHYLHEXYL METHOXYCINNAMATE, SILICA, PVP, CHLORPHENESIN, BHT | 20.0 |
| D Phenonip | (5) PHENOXYETHANOL, BUTYLPARABEN, ETHYLPARABEN, PROPYLPARABEN, METHYLPARABEN | 0.7 |

Preparation:
Phase A is combined apart from the EUSOLEX ® T-S and heated to 80° C. EUSOLEX ® T-S is subsequently stirred in slowly. Phase B is heated to 75° C. and slowly added with stirring to phase A. The EUSOLEX ® UV-PEARLS ™ OMC are then added at 40° C., and phase D is subsequently incorporated. Finally, the mixture is homogenised and cooled with stirring.
Notes:
Viscosity 6000 mPas (Brookfield LV, spindle 4, 60 rpm) at 25° C.
Sources of supply:
(1) MERCK KGAA/RONA ®
(2) Uniqema
(3) Cognis GmbH
(4) Phoenix Chemical
(5) Nipa Laboratorien GmbH

Example 3

Sunscreen Lotion (W/O); SPF 16.7/UVA PF 8.0

| Raw material | INCI | % by wt. |
|---|---|---|
| A EUSOLEX ® T-ECO | (1) TITANIUM DIOXIDE, ALUMINA, SIMETHICONE | 4.0 |
| EUSOLEX ® OCR | (1) OCTOCRYLENE | 7.0 |
| Arlacel P135 | (2) PEG-30 DIPOLYHYDROXYSTEARATE | 2.5 |
| Abil WE 09 | (3) POLYGLYCERYL-4 ISOSTEARATE, CETYL DIMETHICONE COPOLYOL, HEXYL LAURATE | 2.5 |
| Crodafos CES | (4) CETEARYL ALCOHOL, CETEARYL PHOSPHATE | 1.0 |
| Ewalin 1751 | (5) PETROLATUM | 3.0 |
| Cetiol 868 | (6) ETHYLHEXYL STEARATE | 4.0 |
| Miglyol 812 N | (7) CAPRYLIC/CAPRIC TRIGLYCERIDE | 4.0 |
| Dow Corning 345 | (8) CYCLOMETHICONE | 3.0 |
| Dow Corning 200 (100 cs) | (8) DIMETHICONE | 2.0 |
| Paracera W 80 | (9) CERESIN (MICROCRYSTALLINE WAX) | 0.5 |
| Propyl 4-hydroxybenzoate | (1) PROPYLPARABEN | 0.05 |
| B RONACARE ™ ectoin | (1) ECTOIN | 0.1 |
| RONACARE ™ allantoin | (1) ALLANTOIN | 0.2 |
| 1,2-Propanediol | (1) PROPYLENE GLYCOL | 3.0 |
| Sodium chloride | (1) SODIUM CHLORIDE | 0.5 |
| Methyl 4-hydroxybenzoate | (1) METHYLPARABEN | 0.15 |
| Water, demineralised | AQUA (WATER) | 62.2 |

| Raw material | INCI | % by wt. |
|---|---|---|
| C Sun Care Perf. D10316E PM perfume oil | (10) PARFUM | 0.3 |

Preparation:
Phase A is combined apart from the EUSOLEX ® T-ECO and heated to 80° C. EUSOLEX ® T-ECO is slowly stirred into the hot oil phase. Phase B is then heated to 80° C. and slowly added to phase A with stirring. The mixture is carefully homogenised at 50-40° C. in order to enable optimum dispersal of the particles of EUSOLEX ® T-ECO. Phase C is then added at 40° C., and the mixture is cooled with stirring.

Notes:
Viscosity 11,800 mPas (Brookfield RVT, sp. C, 10 rpm) at 26° C.

Sources of supply:
(1) MERCK KGAA/RONA ®
(2) Uniqema
(3) Degussa-Goldschmidt AG
(4) Croda GmbH
(5) H. Erhard Wagner GmbH
(6) Cognis GmbH
(7) Sasol Germany GmbH
(8) Dow Corning
(9) Paramelt
(10) Haarmann & Reimer GmbH

Example 4

Sunscreen Lotion (O/W); SPF 14.9/UVA PF 3.9

| Raw material | INCI | % by wt. |
|---|---|---|
| A EUSOLEX ® T-2000 | (1) TITANIUM DIOXIDE, ALUMINA, SIMETHICONE | 5.0 |
| EUSOLEX ® 2292 | (1) ETHYLHEXYL METHOXYCINNAMATE, BHT | 5.0 |
| Emulium delta | (2) GLYCERYL STEARATE, CETYL ALCOHOL, PEG-75 STEARATE, CETETH-20, STEARETH-20 | 3.3 |
| Eumulgin L | (3) PPG-1-PEG-9 LAURYL GLYCOL ETHER | 0.5 |
| SF 1318 | (4) DIISOSTEAROYL TRIMETHYLOLPROPANE SILOXY SILICATE | 1.5 |
| Crodamol AB | (5) C12-15 ALKYL BENZOATE | 3.0 |
| Crodamol DOA | (5) DIOCTYL ADIPATE | 4.0 |
| Dow Corning 200 (100 cs) | (6) DIMETHICONE | 2.0 |
| B RONACARE ™ ectoin | (1) ECTOIN | 0.1 |
| RONACARE ™ allantoin | (1) ALLANTOIN | 0.2 |
| Pecosil PS-100 | (7) DIMETHICONE COPOLYOL PHOSPHATE | 2.5 |
| 1,3-Butanediol | (1) BUTYLENE GLYCOL | 2.5 |
| Water, demineralised | AQUA (WATER) | 68.9 |
| C Salcare SC 96 | (8) PPG-1 TRIDECETH-6, POLYQUATERNIUM-37, PROPYLENE GLYCOL, DICAPRYLATE/DICAPRATE | 0.47 |
| D Paragon | (9) PROPYLENE GLYCOL, DMDM HYDANTOIN, METHYLPARABEN | 0.73 |
| SUNSAFE L20013W perfume oil | (10) PARFUM | 0.3 |

Preparation:
Phase A is combined apart from the EUSOLEX ® T-2000 and heated to 60° C. EUSOLEX ® T-2000 is slowly incorporated into the molten oil phase. Phase B is heated to 60° C., then phase C is dispersed in with stirring, and subsequently phase A is stirred into phase B/C with vigorous stirring. The mixture is cooled with stirring, and phase D is added at 40° C. The mixture is subsequently homogenised (1 minute with the wand at setting II) and cooled to 25° C. with stirring.

Notes:
pH = 4.3 at 23° C.
Viscosity 7700 mPa · s (Brookfield RVT, sp. C, 10 rpm) at 23° C.

Sources of supply:
(1) MERCK KGAA/RONA ®
(2) Gattefosse GmbH
(3) Cognis GmbH
(4) GE Silicones Holland
(5) Croda GmbH
(6) Dow Corning
(7) Phoenix Chemical
(8) Allied Colloids GmbH
(9) Mcintyre Group, LTD.
(10) Haarmann & Reimer GmbH

Example 5

Luxury Night Cream (W/O)

| Raw material | INCI | % by wt. |
| --- | --- | --- |
| A Liquid paraffin | (1) PARAFFINUM LIQUIDUM (MINERAL OIL) | 10.0 |
| Isolan PDI | (2) DIISOSTEAROYL POLYGLYCERYL-3 DIISOSTEARATE | 4.0 |
| Cutina HR | (3) HYDROGENATED CASTOR OIL | 0.4 |
| Paracera M | (4) MICROWAX | 0.2 |
| Cetiol 868 | (3) ETHYLHEXYL STEARATE | 12.0 |
| B RONACARE ™ ectoin | (1) ECTOIN | 1.0 |
| Glycerol (87% extra pure) | (1) GLYCERIN | 3.0 |
| Preservative | | q.s. |
| Magnesium sulfate 1.05882 heptahydrate | (1) MAGNESIUM SULFATE | 1.0 |
| Water, demineralised | AQUA (WATER) | 68.4 |

Preparation:
Phase A and phase B are warmed separately to 80° C. Phase B is added to phase A with stirring. The mixture is subsequently cooled and homogenised with stirring.
Notes:
Viscosity (23° C.): 32,000 mPa · s (Brookfield RVT, spindle C, 5 rpm, Helipath)
Sources of supply:
(1) MERCK KGAA/RONA ®
(2) Degussa-Goldschmidt AG
(3) Cognis GmbH
(4) Paramelt

Example 6

Winter Face Cream (W/O)

| Raw material | INCI | % by wt. |
| --- | --- | --- |
| A Liquid paraffin | (1) PARAFFINUM LIQUIDUM (MINERAL OIL) | 5.0 |
| Isolan PDI | (2) DIISOSTEAROYL POLYGLYCERYL-3 DIISOSTEARATE | 4.0 |
| Isopropyl palmitate | (3) ISOPROPYL PALMITATE | 8.0 |
| Beeswax bleached | (1) CERA ALBA (BEESWAX) | 1.0 |
| Cutina HR | (3) HYDROGENATED CASTOR OIL | 1.0 |
| Cetyl palmitate | (1) CETYL PALMITATE | 2.0 |
| Cetiol SN | (3) CETEARYL ISONONANOATE | 7.0 |
| B RONACARE ™ ectoin | (1) ECTOIN | 1.0 |
| Glycerol (87% extra pure) | (1) GLYCERIN | 3.0 |
| Preservative | | q.s. |
| Magnesium sulfate heptahydrate | (1) MAGNESIUM SULFATE | 1.0 |
| Water, demineralised | AQUA (WATER) | 67.0 |

Preparation:
Phase A is warmed to 80° C. Phase B is then dissolved with stirring and slowly added to phase A with stirring. The mixture is subsequently homogenised and cooled with stirring.
Notes:
Viscosity (27° C.): 16,000 mPa · s (Brookfield RVT, spindle C, 20 rpm, Helipath)
Sources of supply:
(1) MERCK KGAA/RONA ®
(2) Degussa-Goldschmidt AG
(3) Cognis GmbH

Example 7

Shampoo

| Raw material | INCI | % by wt. |
| --- | --- | --- |
| A RONACARE ™ ectoin | (1) ECTOIN | 1.0 |
| Texapon NSO | (2) SODIUM LAURETH SULFATE | 34.0 |
| Tego Betain L 7 | (3) COCAMIDOPROPYL BETAINE | 10.0 |
| Sodium chloride | (1) SODIUM CHLORIDE | 1.13 |
| Glycerol (87% extra pure) | (1) GLYCERIN | 2.0 |

| Raw material | INCI | % by wt. |
|---|---|---|
| Water, demineralised | AQUA (WATER) | 51.87 |

Preparation:
Phase A is weighed out and stirred until dissolved homogeneously.
Notes:
pH (25° C.): 6.30
Viscosity (28° C.): 1700 mPa · s (Brookfield RVT, spindle B, 10 rpm, Helipath)
Sources of supply:
(1) MERCK KGAA/RONA ®
(2) Cognis GmbH
(3) Degussa-Goldschmidt AG

Example 8

Luxury Body Care (O/W)

| | Raw material | INCI | % by wt. |
|---|---|---|---|
| A | Tego Care 215, pellets | (1) GLYCERYL STEARATE, CETEARETH-15 | 2.0 |
| | Avocado oil | (2) PERSEA GRATISSIMA | 3.0 |
| | Miglyol 812 N | (3) CAPRYLIC/CAPRIC TRIGLYCERIDE | 3.0 |
| | Abil 350 | (1) DIMETHICONE | 0.5 |
| | Lanette 18 | (4) STEARYL ALCOHOL | 1.5 |
| | Carbopol ETD 2050 | (5) CARBOMER | 0.1 |
| B | Glycerol (87% extra pure) | (6) GLYCERIN | 3.0 |
| | RONACARE ™ ectoin | (6) ECTOIN | 1.0 |
| | Preservative | | q.s. |
| | Water, demineralised | AQUA (WATER) | 85.9 |
| C | Sodium hydroxide solution, 10% | (6) SODIUM HYDROXIDE | q.s. |

Preparation:
Phases A and B are warmed separately to 80° C. Phase B is then added to phase A with stirring and homogenised. The mixture is subsequently neutralised and cooled with stirring.
Notes:
pH (25° C.): 5.80
Viscosity (25° C.): 28,000 mPa · s (Brookfield RVT, spindle C, 5 rpm, Helipath)
Sources of supply:
(1) Degussa-Goldschmidt AG
(2) Gustav Heess GmbH
(3) Sasol Germany GmbH
(4) Cognis GmbH
(5) BF Goodrich
(6) MERCK KGAA/RONA ®

Example 9

Protective Baby Care (O/W)

| | Raw material | INCI | % by wt. |
|---|---|---|---|
| A | Liquid paraffin | (1) PARAFFINUM LIQUIDUM (MINERAL OIL) | 5.0 |
| | Emulsogen SRO | (2) RAPESEED OIL SORBITOL ESTERS | 1.0 |
| | Isopropyl palmitate | (3) ISOPROPYL PALMITATE | 6.0 |
| | Jojoba oil | (4) BUXUS CHINENSIS (JOJOBA OIL) | 2.0 |
| | Miglyol 812 N | (5) CAPRYLIC/CAPRIC TRIGLYCERIDE | 4.0 |
| | Soya oil | (4) GLYCINE SOJA (SOYBEAN OIL) | 3.0 |
| | Carbopol ETD 2001 | (6) CARBOMER | 0.5 |
| B | Hostapon CLG | (2) SODIUM LAUROYL GLUTAMATE | 0.6 |
| | Titriplex III | (1) DISODIUM EDTA | 0.1 |
| | Citric acid monohydrate | (1) CITRIC ACID | 0.03 |
| | Glycerol (87% extra pure) | (1) GLYCERIN | 3.0 |
| | Preservative | | q.s. |
| | RONACARE ™ ectoin | (1) ECTOIN | 1.0 |
| | Water, demineralised | AQUA (WATER) | 73.07 |

-continued

| Raw material | INCI | % by wt. |
|---|---|---|
| C Sodium hydroxide solution, 10% | (1) SODIUM HYDROXIDE | 0.7 |

Preparation:
Phases A and B are each stirred well. Phase B is then added to phase A with stirring and homogenised. The mixture is subsequently neutralised using phase C and stirred until ready.
Notes:
pH (25° C.): 6.00
Viscosity (25° C.): 27,000 mPa · s (Brookfield RVT, spindle C, 5 rpm, Helipath)
Sources of supply:
(1) MERCK KGAA/RONA ®
(2) Clariant GmbH
(3) Cognis GmbH
(4) Gustav Heess GmbH
(5) Sasol Germany GmbH
(6) BF Goodrich

Example 10

Sun Complete (O/W)

| Raw material | INCI | % by wt. |
|---|---|---|
| A EUSOLEX ® 2292 | (1) ETHYLHEXYL METHOXYCINNAMATE, BHT | 4.0 |
| EUSOLEX ® 4360 | (1) BENZOPHENONE-3 | 1.0 |
| Tego Care 215, pellets | (2) GLYCERYL STEARATE, CETEARETH-15 | 2.5 |
| Cetiol V | (3) DECYL OLEATE | 5.0 |
| Isopropyl palmitate | (3) ISOPROPYL PALMITATE | 5.0 |
| Abil 350 | (2) DIMETHICONE | 0.5 |
| Lanette 18 | (3) STEARYL ALCOHOL | 2.0 |
| Carbopol ETD 2050 | (4) CARBOMER | 0.1 |
| B Glycerol (87% extra pure) | (1) GLYCERIN | 3.0 |
| RONACARE ™ ectoin | (1) ECTOIN | 1.0 |
| Preservative | | q.s. |
| Water, demineralised | AQUA (WATER) | 75.9 |
| C Sodium hydroxide solution, 10% | (1) SODIUM HYDROXIDE | q.s. |

Preparation:
Phases A and B are warmed separately to 80° C. Phase B is then added to phase A with stirring and homogenised. The mixture is subsequently neutralised using sodium hydroxide solution and cooled with stirring.
Notes:
pH (20° C.): 5.90
Viscosity (26° C.): 24,000 mPa · s (Brookfield RVT, spindle C, 5 rpm, Helipath)
SPF (Diffey method): 8
Sources of supply:
(1) MERCK KGAA/RONA ®
(2) Degussa-Goldschmidt AG
(3) Cognis GmbH
(4) BF Goodrich

Example 11

Lip Gloss (W/O)

| Raw material | INCI | % by wt. |
|---|---|---|
| A COLORONA ® Imperial Red | (1) MICA, CI 77891 (TITANIUM DIOXIDE), CI 73360 (D&C RED NO. 30) | 5.0 |
| OXYNEX ® K liquid | (1) PEG-8, TOCOPHEROL, ASCORBYL PALMITATE, ASCORBIC ACID, CITRIC ACID | 0.1 |
| Magnesium stearate | (1) MAGNESIUM STEARATE | 1.5 |
| Sisterna A 10E-C | (2) SUCROSE TETRASTEARATE TRIACETATE | 15.0 |

-continued

| Raw material | INCI | % by wt. |
|---|---|---|
| Castor oil | (3) RICINUS COMMUNIS (CASTOR OIL) | 55.3 |
| Aerosil R 972 | (4) SILICA | 1.0 |
| Rubis Covapate W 4765 | (5) RICINUS COMMUNIS (CASTOR OIL), CI 15850 (D&C RED NO. 7 CALCIUM LAKE) | 0.2 |
| Tendresse 75418C perfume oil | (6) PARFUM | 0.2 |
| B RONACARE ™ ectoin | (1) ECTOIN | 1.0 |
| Glycerol (87% extra pure) | (1) GLYCERIN | 5.0 |
| Magnesium sulfate heptahydrate | (1) MAGNESIUM SULFATE | 0.7 |
| Water, demineralised | AQUA (WATER) | 15.0 |
| Preservative | | q.s. |

Preparation:
The dye is stirred into castor oil. The remaining ingredients are subsequently incorporated, and the mixture is heated to 75-80° C. Phase B is mixed and warmed to 75-80° C. Phase B is then added to phase A with stirring, homogenised and cooled to room temperature with stirring.
Notes:
Viscosity (24° C.): 350,000 mPa · s (Brookfield RVT, spindle D, 5 rpm, Helipath)
Sources of supply:
(1) MERCK KGAA/RONA ®
(2) Sisterna C. V.
(3) Henry Lamotte GmbH
(4) Degussa AG
(5) Les Colorants Wackherr
(6) Haarmann & Reimer GmbH

Example 12

Body Milk (W/O)

| Raw material | INCI | % by wt. |
|---|---|---|
| A Liquid paraffin | (1) PARAFFINUM LIQUIDUM (MINERAL OIL) | 8.0 |
| OXYNEX ® K liquid | (1) PEG-8, TOCOPHEROL, ASCORBYL PALMITATE, ASCORBIC ACID, CITRIC ACID | 0.05 |
| Dragosan W/O | (2) SORBITAN ISOSTEARATE, HYDROGENATED CASTOR OIL, CERESIN, CERA ALBA, PARAFFINUM LIQUIDUM | 1.5 |
| Olive oil refined | (3) OLEA EUROPAEA | 5.0 |
| Isopropyl palmitate | (4) ISOPROPYL PALMITATE | 5.0 |
| Coconut oil refined | (3) COCOS NUCIFERA | 1.0 |
| Dow Corning 200 fluid (350 cs) | (5) DIMETHICONE | 3.0 |
| Vaseline | (6) PETROLATUM | 1.0 |
| B Water, demineralised | AQUA (WATER) | 68.25 |
| Glycerol (87% extra pure) | (1) GLYCERIN | 5.5 |
| Magnesium sulfate heptahydrate | (1) MAGNESIUM SULFATE | 0.7 |
| RONACARE ™ ectoin | (1) ECTOIN | 1.0 |
| Preservative | | q.s. |
| C Perfume oil | PARFUM | q.s. |

Preparation:
Phase A and phase B are warmed separately to 80° C. Phase B is then incorporated into phase A with homogenisation. The mixture is cooled to 65° C. with stirring and re-homogenised. The mixture is perfumed with phase C at 35° C.
Notes:
Viscosity: 14,900 mPa · s (Brookfield RVT, spindle C, 10 rpm, Helipath), 25° C.
Sources of supply:
(1) MERCK KGAA/RONA ®
(2) Dragoco Gerberding & Co. AG
(3) Gustav Heess GmbH
(4) Cognis GmbH
(5) Dow Corning
(6) Schümann Sabol

Example 13

Lip Fix

| Raw material | INCI | % by wt. |
|---|---|---|
| RONACARE ™ ectoin | (1) ECTOIN | 0.5 |
| Ethanol 96% extra pure | (1) ALCOHOL | 70.0 |
| Ethocel | (2) ETHYLCELLULOSE | 1.0 |
| RONACARE ™ CPC | (1) CETYLPYRIDINIUM CHLORIDE | 0.15 |
| Water, demineralised | AQUA (WATER) | 28.35 |

Preparation:
The ethanol, water and RONACARE ™ CPC are initially introduced, and the thickener is scattered in with stirring. The mixture is stirred until a clear solution is formed, and the RONACARE ™ ectoin is added and dissolved with stirring.

Notes:
pH: 6.20 (23° C.)
Sources of supply:
(1) MERCK KGAA/RONA ®
(2) Dow Chemical

Figure 1:
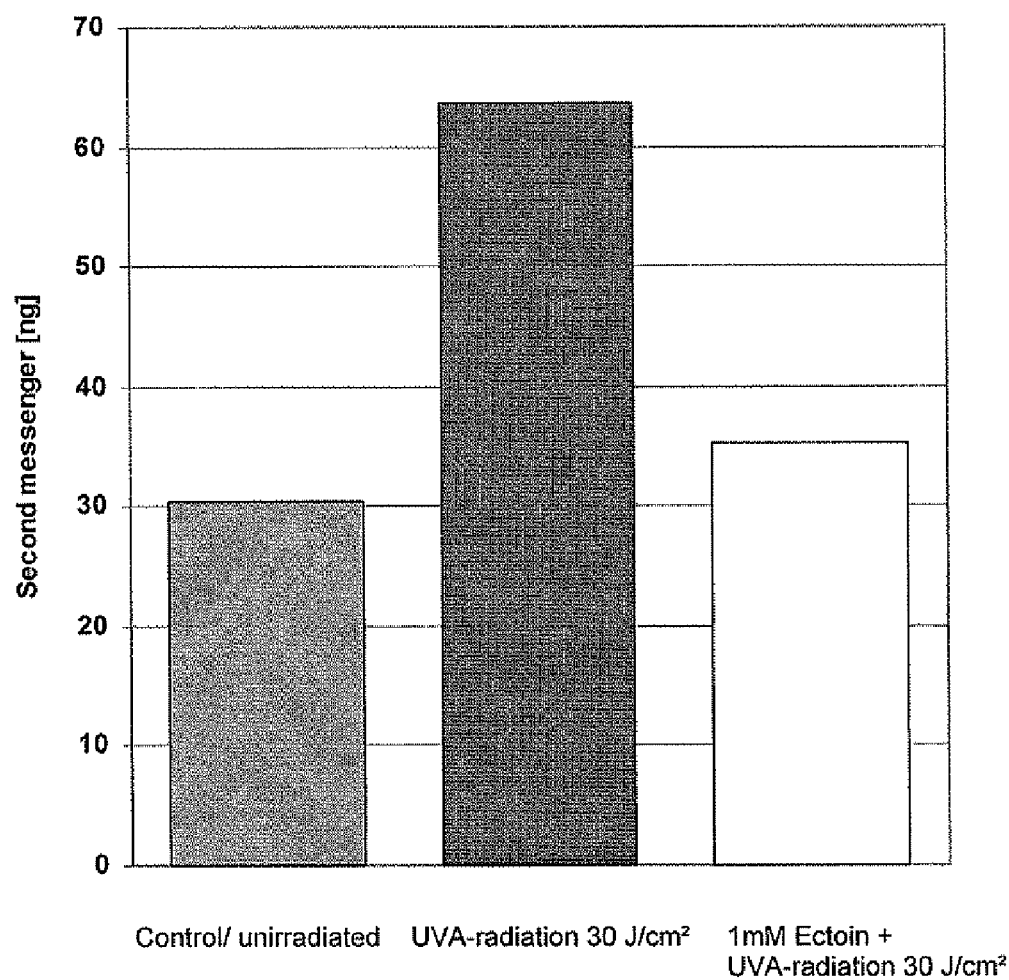
FIG. 1: UVA-induced second messenger release in keratinocytes after pretreatment with ectoin for 24 hours.
Figure 2:
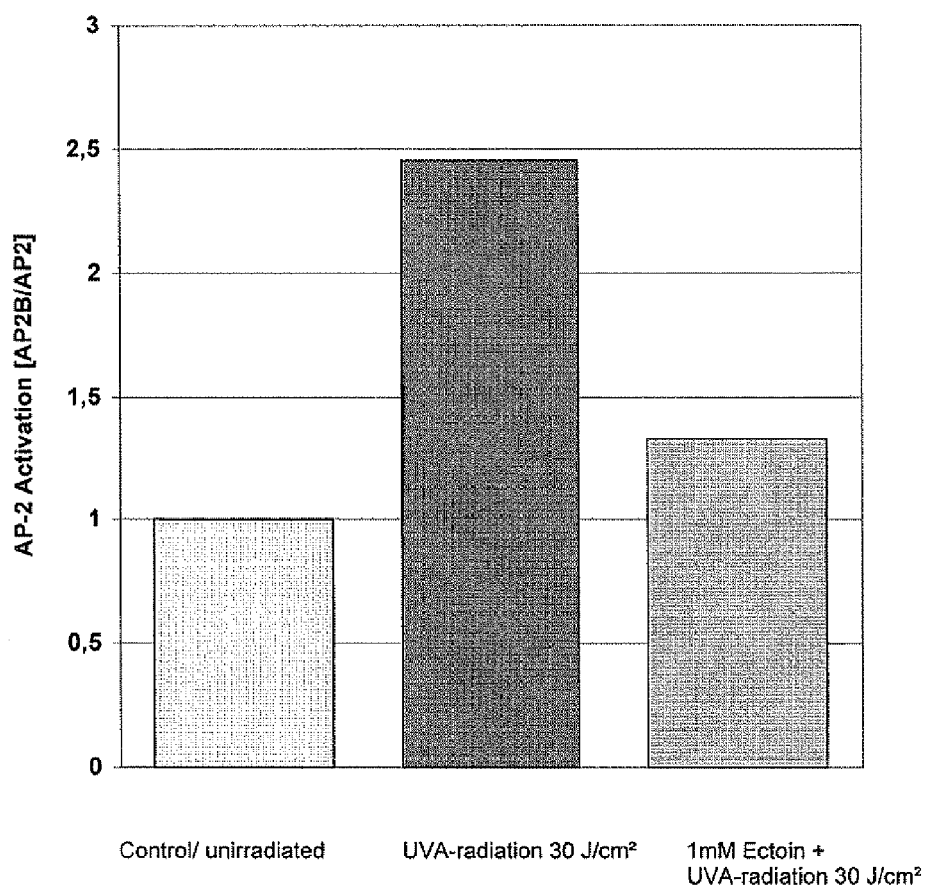
FIG. 2: Ectoin- and UVA-induced AP-2 activation
Figure 3:
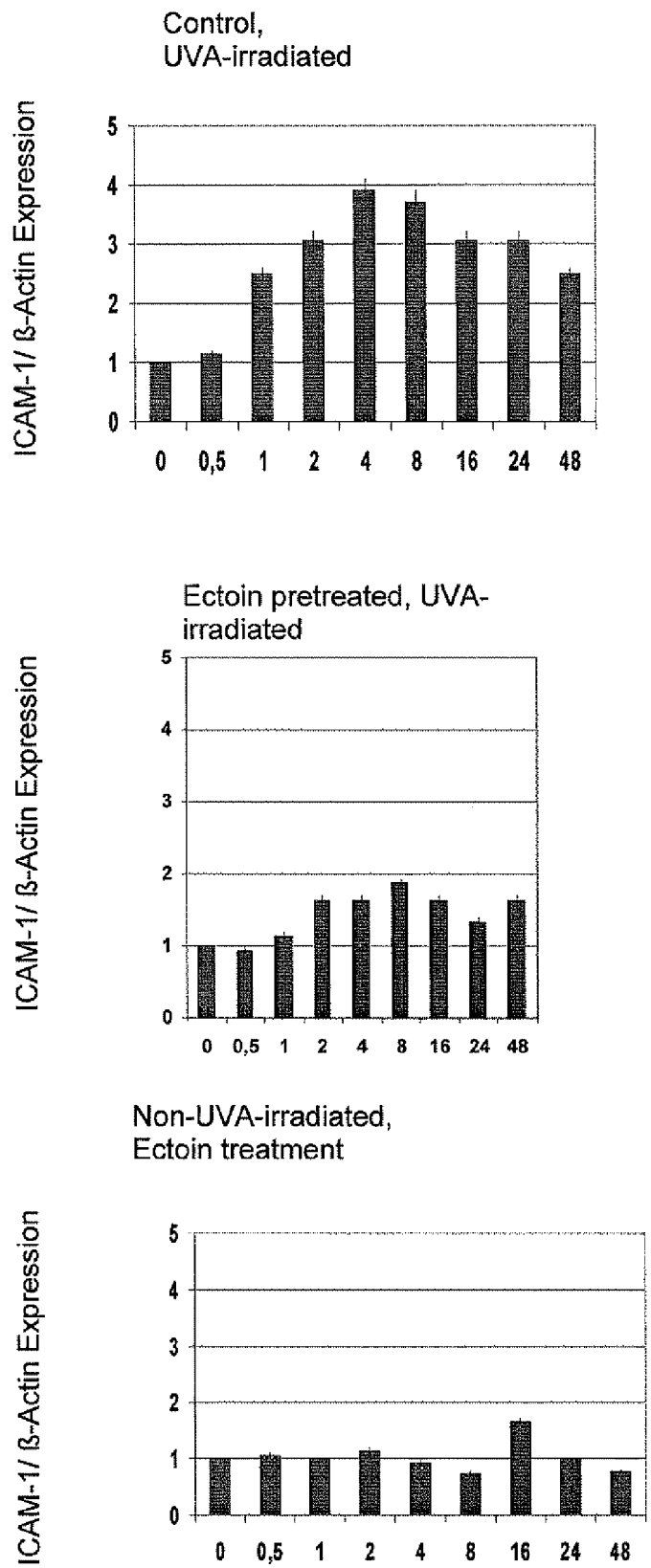
FIG. 3: Inhibition of UVA-induced ICAM-1 gene expression by ectoin
Figure 4:
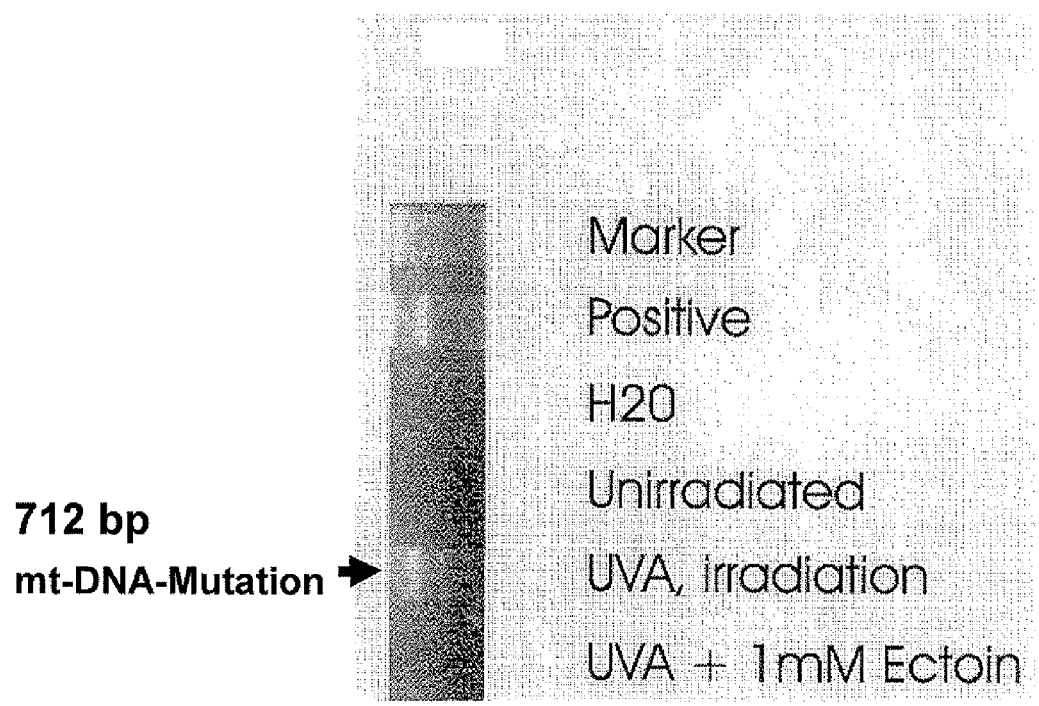
FIG. 4: Effect of ectoin on the UVA-induced formation of mt-DNA mutations

The invention claimed is:

1. A method for the protection of human skin against wrinkling, comprising administering to a subject in need thereof a compatible solute, which is of formula Ia or Ib

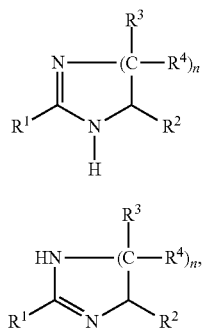

or a physiologically acceptable salt thereof,
$R^1$ is H or alkyl,
$R^2$ is H, COOH, COO-alkyl or CO—NH—$R^5$,
$R^3$ and $R^4$ are each, independently of one another, H or OH,
n is 1, 2 or 3,
alkyl is an alkyl radical having from 1 to 4 carbon atoms, and
$R^5$ is H, alkyl, an amino acid residue, a dipeptide radical or a tripeptide radical.

2. A method according to claim 1, wherein the compatible solute of formula Ia or Ib is in the form of a cosmetic, dermatological or pharmaceutical composition.

3. A method according to claim 1, wherein the compound of formula Ia or Ib is (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid.

4. A method according to claim 1, wherein the proportion of compatible solute of formula Ia or Ib in a composition administered is 0.001 to 50% by weight, based on the composition as a whole.

5. A method for the protection of the human skin against wrinkling, comprising administering to a subject in need thereof a compatible solute, which is of formula Ia or Ib

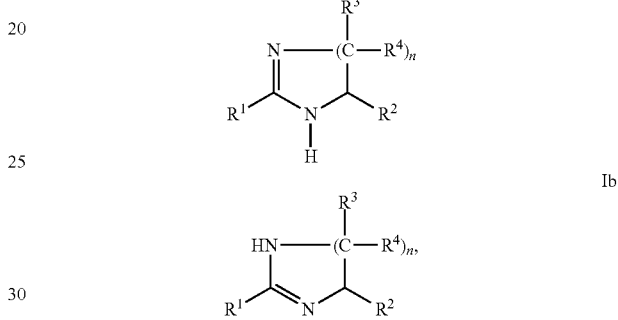

or a physiologically acceptable salt thereof,
$R^1$ is H or alkyl,
$R^2$ is H, COOH, COO-alkyl or CO—NH—$R^5$,
$R^3$ and $R^4$ are each, independently of one another, H or OH,
n is 1, 2 or 3,
alkyl is an alkyl radical having from 1 to 4 carbon atoms, and
$R^5$ is H, alkyl, an amino acid residue, a dipeptide radical or a tripeptide radical.

6. A method according to claim 1, wherein an isolated stereoisomeric form of a compound of formula Ia or Ib is administered.

7. A method according to claim 5, wherein the compatible solute of formula Ia or Ib is in the form of a cosmetic, dermatological or pharmaceutical composition.

8. A method according to claim 5, wherein the compound of formula Ia or Ib is (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid.

9. A method according to claim 5, wherein the proportion of compatible solute of formula Ia or Ib in a composition administered is 0.001 to 50% by weight, based on the composition as a whole.

10. A method according to claim 5, wherein an isolated stereoisomeric form of a compound of formula Ia or Ib is administered.

* * * * *